United States Patent [19]

Isselstein et al.

[11] Patent Number: 4,593,567
[45] Date of Patent: Jun. 10, 1986

[54] ELECTROMAGNET TRANSDUCER

[75] Inventors: Fritz Isselstein, Meerbusch; Ernst Luhn, Wuppertal; Gunther Coen, Dusseldorf; Dietmar Oberhoff, Wermelskirchen; Roland Keck, Dusseldorf, all of Fed. Rep. of Germany

[73] Assignee: Betriebsforschungsinstitut VDEH Institut for Angewandete Forschung GmbH, Dusseldorf, Fed. Rep. of Germany

[21] Appl. No.: 645,299

[22] Filed: Aug. 29, 1984

[30] Foreign Application Priority Data

Sep. 2, 1983 [DE] Fed. Rep. of Germany ....... 3331727

[51] Int. Cl.$^4$ ............................................. G01N 29/04
[52] U.S. Cl. .................................................... 73/643
[58] Field of Search ................................. 73/643, 159

[56] References Cited

U.S. PATENT DOCUMENTS 3,850,028 11/1974 Thompson et al. ................... 73/643
4,434,663 3/1984 Peterson et al. ...................... 73/643
4,522,071 6/1985 Thompson ............................ 73/643

FOREIGN PATENT DOCUMENTS 0794491 1/1981 U.S.S.R. ............................... 73/643
0868561 9/1981 U.S.S.R. ............................... 73/643

Primary Examiner—Anthony V. Ciarlante
Attorney, Agent, or Firm—Holman & Stern

[57] ABSTRACT

There is disclosed an electromagnetic transducer for the transmission and reception of ultrasonic waves in the touchless testing of metal workpieces, particularly made of steel, in the shape of sheet and strip material. The transducer is arranged for continuous testing, particularly as applied to continuously advancing material, by wavelength spectroscopy and particularly modal spectroscopy of received ultrasonic waves. To this end, the transducer comprises a pair of transducer segments each of which has a set of mutually parallel conductor tracks formed on a substantially planar printed circuit board in which the frequencies and wavelengths for each segment can be preset in a matrix logic circuit having a short time sequence. The conductor tracks comprise windings arranged to be connected for operation through a set of switching elements in such a manner as to produce in various switching states of the switching elements a plurality of wavelengths for each frequency. The wavelengths being proportionally related to each other by small integral numbers.

12 Claims, 8 Drawing Figures

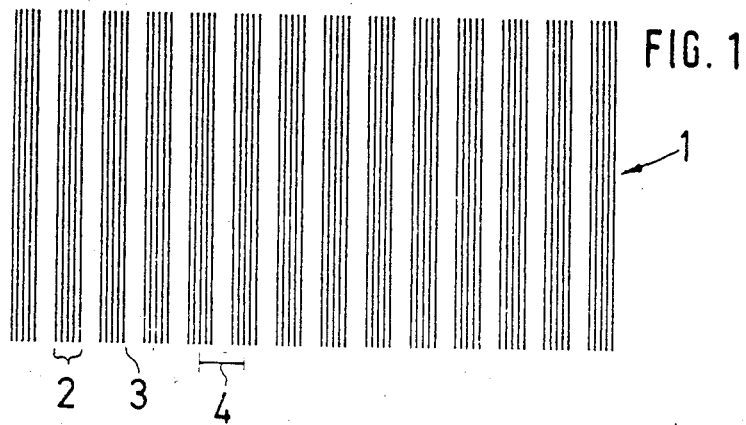
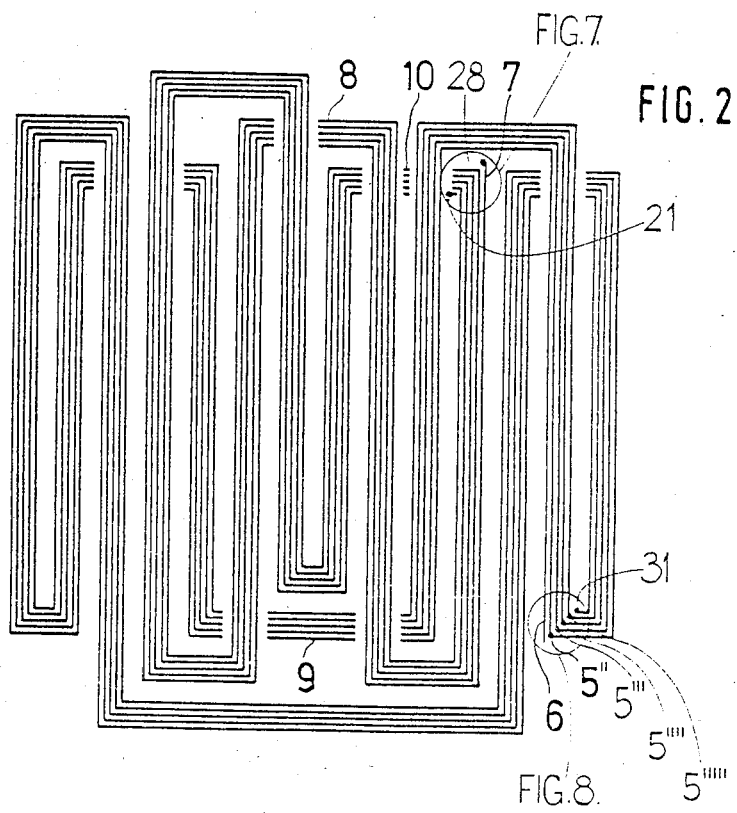

ELECTROMAGNET TRANSDUCER

BACKGROUND OF THE INVENTION

The invention relates to an electromagnetic transducer for the transmission and reception of ultrasonic waves in the touchless testing of metal workpieces, particularly but not exclusively flat strip or sheet metal or ferritic or austenitic steel comprising at least one transducer element having a plurality of mutually parallel conductor tracks formed on a substantially planar printed circuit board.

A transducer of this kind is described in the paper by H. Licht, TH Aachen, 1973 entitled "A potential method of touchless excitation and reception of Lamb waves in electrically conductive plates by a mode-selective electrodynamic transducer system". In order to be able to apply a data-providing mode-spectroscopy to thin work pieces, this previously known transducer comprises exchangeable circuit boards with relatively different conductor-line arrangements or patterns whereby the respective wavelength is determined. Testing frequency on the other hand is continuously adjustable. Whilst this method eventually provides a positive test result from which information can be obtained it is extremely time-taking. In particular, it does not allow continuous mode-spectroscopic testing of material to be made. Besides, there are other interfering influences. Furthermore, there is a limitation in respect of the test samples in the form of thin plates and correspondingly in respect of waveform in the shape of Lamb waves.

SUMMARY OF THE INVENTION

The electromagnetic transducer according to the invention is also designed to enable in ferromagnetic materials the stimulation and the reception of ultrasonic waves by virtue of the Lorentz-effect and of the magnetostrictive-effect, both of which are reversible, and thus affording the possibility of transmission and reception. With para- or diamagnetic metals, however, there is no magnetorestrictive effect and neither does this effect appear above the Curie point. The Lorentz effect alone will also enable transmission and reception. The respective shear wave mode is then obtained, with a predetermined band thickness and wavelength, by appropriate frequency choice in accordance with the presumably familiar dispersion diagram. Besides, in testing thick workpieces other wave types (longitudinal, transversal and Rayleigh) are also to be stimulated and received.

Where application is limited to the Lorentz-effect the alternating current which is fed into the transmitter-transducer creates an alternating electromagnetic field whereby eddy-currents are induced in the surface of the workpiece. By interaction of the eddy current with a horizontal constant magnetic field the Lorentz forces influence the free electrons and thereby indirectly also the metal lattice of the test object. On the basis of their spatial and time-periodity they stimulate ultrasonic waves of which the wavelength is predetermined by the transducer geometry and the frequency by the applied alternating current.

In the case of ferritic materials, the eddy-currents induced in the workpiece surface by the transmitter transducer generate a magnetic alternating field which is superimposed on the imprinted constant magnetic field. The resulting modulated magnetic field provokes local magnetostrictive expansions of the ferritic material and thereby generates an ultrasonic wave at predetermined frequency and wavelength.

In touchless ultrasonic material testing it is important, besides the detection and localisation of faults, also to allow a qualitative classification of the material to be made by type of fault, size and position thereof, for example by picking up a crack or a voluminous fault area, its characteristic linear measurements and the orientation of the main fault axes relative to the direction of sound propagation.

Since, according to the prior art, guided waves are used a modal spectroscopy allows the classification and evaluation of faults by using algorithms. The same fault point is here successively addressed in multiplex operation in several different modes and for each mode several different wavelengths are successively applied. The fact that in the diffraction of a guided wave the reflection factor depends not only as with a free or unconstrained wave on wavelength, characteristic linear dimensions of the fault, nature and orientation of the fault, but also varies with the goemetrical parameters of the wave conductor and in relation with the material used, may then be utilized for a modal spectroscopic fault classification.

However, the use of free ultrasonic waves in the form of longitudinal or transversal waves, subject to the application of several different wavelengths in multiplex operation, also offers at any rate the possibility of classifying the detected faults by normal spectroscopy which is not to be excluded in the context of this invention.

The object of the invention resides in providing an electromagnetic transducer whereby spectroscopy, particularly but not exclusively modal spectroscopy, of the test piece may be realized at a very short time sequence. Primarily, but not exclusively, due to this aptitude the new electromagnetic transducer shall be suited for the ultrasonic testing of continuously advancing sheet or strip material.

According to this invention there is provided an electromagnetic transducer for the transmission and reception of ultrasonic waves in the touchless testing of metal workpieces by wavelength spectroscopy comprising at least one transducer segment having a plurality of mutually parallel conductor tracks formed on a substantially plane printed circuit board in which the frequencies and wavelengths for each segment can be preset in a matrix logic circuit having a short time sequence and in which the conductor tracks comprise windings arranged to be connected for operation through a set of switching elements in such a manner as to produce in various switching states of said switching elements a plurality of wavelengths for each frequency, said wavelength being proportionally related to each other by small integral numbers.

In this fashion a transducer is obtained in which the frequencies and wavelengths can be preset via a matrix circuit and the individual operations can be executed within the frequency-wavelength matrix by activation of the switching elements. The means applied to this end are electronic means, such as for example electronic switches, and per se known. Thus, in an electromagnetic transducer arranged in accordance with the invention, the switches may be integrated in the converter so that the matrix operations can be made fully electronically, and therefore at the same time in a sufficiently short time sequence.

Although the times which are needed are extremely short there are nevertheless certain practical limitations in respect of the matrix operations which must be executed. For example it is possible to manage with from 4 to 8 different frequencies whilst the ratios of wavelengths as a rule are merely 2, 3 and 5 or 3, 4 and 5. Only in very exceptional cases will there be any need to consider also the ratio number 7 in order thereby to arrive at 4 different wavelengths.

A far-reaching adaptation to the dimensions of the tested workpieces and also to the types of material thereof is obtained by reason of the fact that the conductor paths are in each case multi-winding tracks and that they are equi-distantly spaced. Conveniently the winding parts are also relatively equi-distantly spaced. This enables adherance to precisely pre-set geometrical configurations which determine the individual wavelengths. In practice such conductor tracks or paths can be very accurately produced by application or photolithographic techniques.

Still further reaching adaptation in the above sense is afforded by a polarity arrangement of the conductor tracks in such a fashion as to obtain selectively a coil or a meander.

In order to obtain maximum efficiency of the transducer it is advisable to smooth the AC impedance thereof which is known to depend on frequency. To this end the conductor tracks are provided with appropriately spaced junctions. In this way the number of effectively used windings may be varied and a constant transducer impedance can be obtained. The multi-winding conductor which incidentally produce a high inductance on the receiver side, are particularly suited for this purpose.

For achieving a directional effect it is further advisable to provide two laterally spaced segments, one above the other, which are basically of identical configuration. They are conveniently laterally offset relative to each other by a fraction of less than $\frac{1}{2}$ of the wavelength. Such segments may be operated with a phase difference by means of a controllable circuit. For a given frequency it is therefore possible to delay the generator signal for a segment electrically by the same fraction of the period as applies in respect of the wavelengths. As a result of such arrangement, the sound fields transmitted by the transmitter transducers will mutually overlap constructively in one direction and destructively in the opposite direction thereby producing the desired beamed or directional effect of the transmitter.

The magnetic forces which occur during operation are very great. Particularly when working with continuously advancing strip material it is important to make sure that the relative distance between converter and test piece will be maintained despite the strong magnetic field. Conveniently this is successfully achieved by means of electrically conductive rollers of plastics material which roll in conductive contact on the tested work piece and connect it at the same time with the earth terminal of the receiving transducer.

Fault detection occurs conveniently with the aid of a digital signal detector circuit, the received signal being then processed in accordance with claim 7. This affords the facility, in particular, of transmitting and receiving at a correspondingly high test-sequence frequency or correspondingly short time sequence so as to achieve simultaneously fully automatic fault-location and classification.

The earlier mentioned photolithographic technique is conveniently applied in the context of this invention in such a way that photolithographically structured conductor tracks are vapour-deposited in the form of metal lines or tracks on an electrically and magnetically nonconductive basis material or substrate. These metal tracks preferably consist of aluminum if Si-monocrystal platelets are used as basis material. Such an arrangement provides a special advantage in respect of testing hot sheet or strip material because the new converter is then also completely thermally reliable even under extreme service conditions.

The winding parts of the conductor tracks are relatively connected in different fashions depending on designed wavelength and polarity. This does not preclude the possibility of intersecting, or crossing conductors. Insulation in the region of intersection, or at the crossing points may then be provided in a very simple manner by arranging for the crossing conductors to be on the respective other side of the substrate.

BRIEF DESCRIPTION OF THE DRAWINGS

This invention will now be described in more detail, by way of example, with reference to the accompanying drawings, in which:

FIG. 1 is a schematic representation of the as yet uncompleted segment construction of a transducer embodying this invention;

FIG. 2 shows the transducer connected as a meander;

DETAILED DESCRIPTION OF THE INVENTION

FIG. 1 shows a segment consisting of conductor tracks 2, only one of which has been provided with the reference number. In each conductor track 2, 5 windings are realized, one of which is indicated t 3. The mean distance of the conductor tracks is indicated at 4. This as well as the relative spacing of the winding parts 3 are constant. It is therefore possible to realise highly differentiated geometrical configurations with this new transducer.

To illustrate this point we describe the example of a transducer with $l=2$ wavelengths. Assuming a winding number $n=5$, a period number $m=2$ and the wavelengths $\lambda_1 = 6$ mm and $\lambda_2 = 9$ mm, the configuration represented in FIG. 2 would be obtained with a meander-shaped axially symmetrical polarity arrangement. With a coil-shaped polarity arrangement one would obtain the picture shown in FIG. 3.

Figure 3:
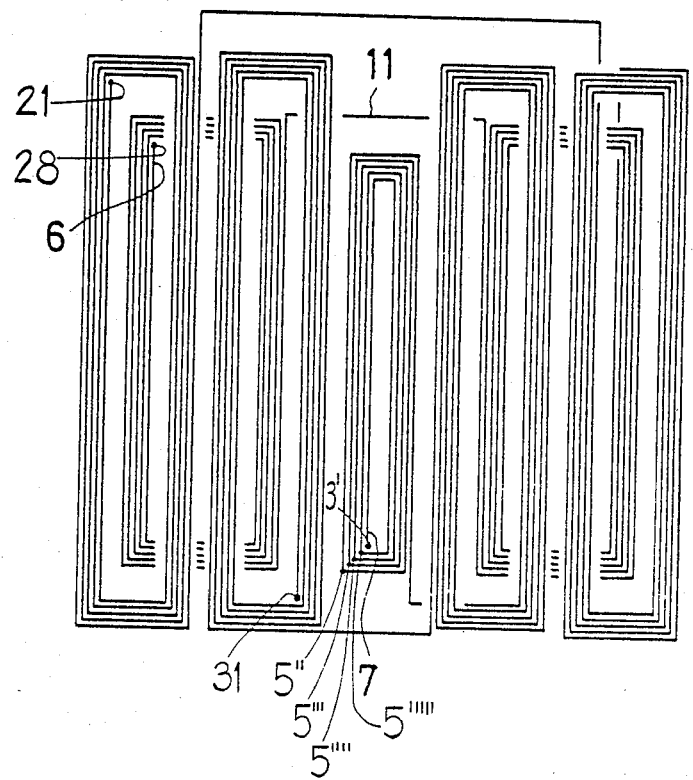
FIG. 3 shows the transducer connected as a coil.

The practical embodiment corresponds to the graphically illustrated configurations according to FIGS. 2 and 3, with this difference, that in the drawings a magnification scale of 1:5 was chosen. The arrangement may also be such that several wavelengths ($l>2$) are realized, also with other winding numbers n and other even numbered period numbers ($m>2$), the wavelength ratios being with the parameters of the present invention of small, integral numbers ($\lambda_1:\lambda_2:\lambda_3 \ldots = p_1:p_2:p_3 \ldots$)

A limitation arises, incidentally, from the fact that the length L of the converter (without the margin widths) is defined by the product.

$$L = \frac{n}{2} \cdot \lambda_1 \cdot \prod_{i=2}^{l} p_i.$$

Adaptation or tuning of the transducer in respect of wave impedance is obtained by using junctions or the converter tracks. FIG. 2 shows junctions 5 of this kind whereby the frequency response curve can be smoothed.

FIG. 2 also shows the provision of two laterally spaced meanders 6,7 which are nested. FIG. 3 also shows the conductor track systems 6, 7 which in this case are coils.

Figure 4:
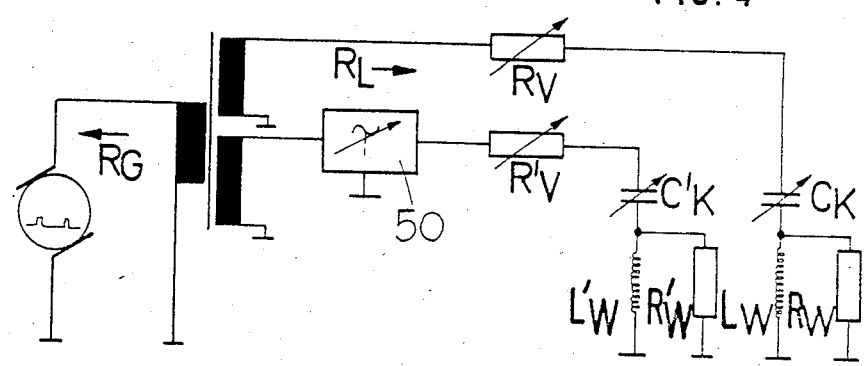
FIG. 4 illustrates the power supply of the transducer including the delay circuit.
Figure 5:
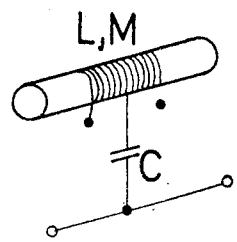
FIG. 5 shows an elemental component of the delay circuit.

The current supply for segments $L_W$, $L'_W$ is shown in FIG. 4. The output of generator G is split up in the output-splitter transmitter in order that both segments may be driven by a single generator. In a given practical example, the output is 36 kW. The transducers which are formed by the conductor track systems are connected with the aid of the adjustable resistors $R_V$ and $R'_V$ and capacitors $C_K$ and $C'_K$ one of which is further preceded by a controllable delaying circuit 50 as may be observed in the lower line of FIG. 4 between the transmitter and the resistor $R'_V$. In this way the generator signal for each segment can be delayed by a fraction of less than ½ of the time period with a given set of frequencies. The sound fields of the transmitter transducer will therefore mutually overlap to provide a directional or beaming effect as hereinbefore described. A component element of the delay circuit is more fully illustrated in FIG. 5. The windings here consists of enamel copper wire wound on an electrically and magnetically non-conductive body. With a suitable choice of data for L,M (opposite inductivity) and C it is possible to set the desired time delay in this sytem. If one of the units according to FIG. 5 should not suffice it is possible to combine several such components in a unit.

Conveniently the delay times which can be set with the aid of the above described delay circuit 50 are graded in binary steps. The delay times may be preselected either manually or by computer control. In view of the fact that the voltages in the transducer are quite substantial namely of the order of 1,000 to 3,000 V, the output switches must be of high-tension-resistant construction. Reflexions at unused parts are avoided in the proposed circuitry. The wave impedance or frequency-reresponse characteristic of the delaying circuit 50 has a value RG and is therefore adapted to inherent generator impedance as well as to the load. All the components of the circuit have a binary grading or stepping and can be driven manually or via computer.

Figure 6:
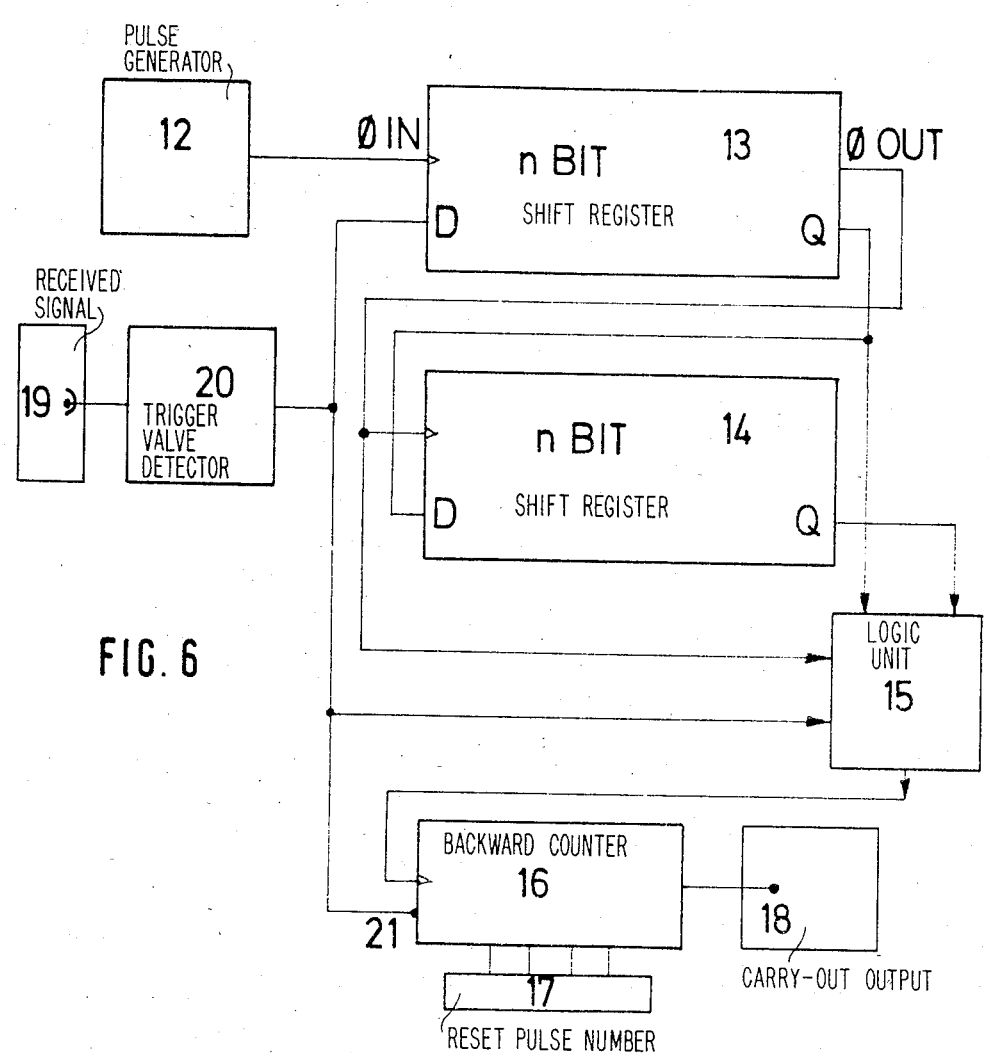
FIG. 6 shows the digital signal detection circuit.

The earlier mentioned digital signal detector circuit according to FIG. 6 is driven by a pulse generator 12 which issues a constant number of pulses per scan. These pulses are applied as clock pulses to serially connected shift registers 13 and 14. The detected received signal is applied as digital value of one bit length to the data input of the shift register unit. Thus a "1" will appear in the shift register when the trigger value which is monitored by the trigger-value detector 20 is exceeded by the received signal 19. In each of the two shift registers 13, 14 one scan is stored. Due to the serial arrangement of the registers at the end of a scan the scan which has just terminated and the preceding one have been stored. By means of the succeeding logic unit 15 it is possible to compare three scans with each other. Since the shift timing is included in the comparison a number of pulses will be obtained as a measure for the duration of overlap. A backward counter 16 set over input 21 counts these pulses. If its preset pulse number 17 is exceeded the carry-out output 18 of the backward counter is briefly activated and this corresponds to a discrimination of the received signal 19 as an ultrasonic signal.

The pulse number setting for a wired transducer set is fixed. It corresponds to the minimum pulse number, less "1" for the overlap time with ultrasonic signals. Since here an ultrasonic signal must appear at least in three successive scans in order to be detected a correspondingly large test-sequence frequency must be selected. If silicon-monocrystal platelets are used in the converter according to the invention, the following process steps will be applied, for example:

1. Production of a silicon-monocrystal
2. Cutting out a thin (d=200 μm) silicon wafer with defined crystal orientation ("wafer");
3. Oxidizing the wafer surface;
4. Applying a photo-film (UV-light-sensitive organic polymer);
5. Making a photo-mask (glassplate with converter structure applied);
6. Photolithographical processing to open up specific faces in the oxide or in the silicon by means of isotropic or anisotropic etching media;
7. Producing contacts and conductor tracks by vapour deposition (or sputtering or bonding);
8. Coating wafer with protective layers ($SiO_2$, $SiN_4$ or the like);

The application of a thin film coating foil entails, for example, the following process steps:

1. selecting a flexible substrate to function as a "carrier" or converter body;
2. simple coating through a mask pressed against said substrate;
3. photolithographic processing involving the following intermediate steps: providing the coated substrate with a photoenamel; exposing the photo-enamel; developing the photo-enamel; etching the coating; removing residual enamel;
4. applying an insulating coat of parylene C (polymer) coating)

Using either of these two methods for making the electromagnetic converter coils it is possible:

1. to construct the transmitter transducer by appropriate choice of number, width, thickness and spacing of the conductor tracks—in such a way that the output which is consumed in the transformed impedance of the tested object will have a high and wide maximum in the respective desired frequency range relative to the maximum output of the generator and that the reactance of the coils can be tuned to series resonance at the respective working frequency by additional inclusion of capacitors in the circuit;
2. to construct the receiver transducer—by appropriate choice of number, width, thickness and spacing of the conductor tracks—in such a way that the conductor track number is limited in the upward sense only in as much as the frequency of the inherent resonance of the segments must be above the respective desired frequency range and that the reactance of the segments can be tuned to parallel resonance at the respective working frequency by additional inclusion of capacitors in the circuit.

FIG. 2 shows some mutually crossing conductors of which those numbered 8, 9 and 10 are characteristic. In a coil arrangement according to FIG. 3 some individual winding parts 11 may also be considered for crossing points. As already mentioned, such intersecting or crossing winding parts are best arranged on the backside of the substrate or basis material.

As already mentioned, FIG. 1 represents the schematic, but as yet uncompleted segment structure of the transducer. By means of corresponding windings of which this segment structure represents a section it is possible selectively to obtain a meander winding according to FIG. 2 or a coil winding according to FIG. 3. In both cases the conductor paths 2 comprise winding parts 3 which are adapted to be connected, by activation applied by switching means, in such a way as to produce for each frequency in several switching states wavelengths in the ratios of small integral numbers. The switching elements required for this purpose are shown in FIGS. 7 and 8.

Figure 7:
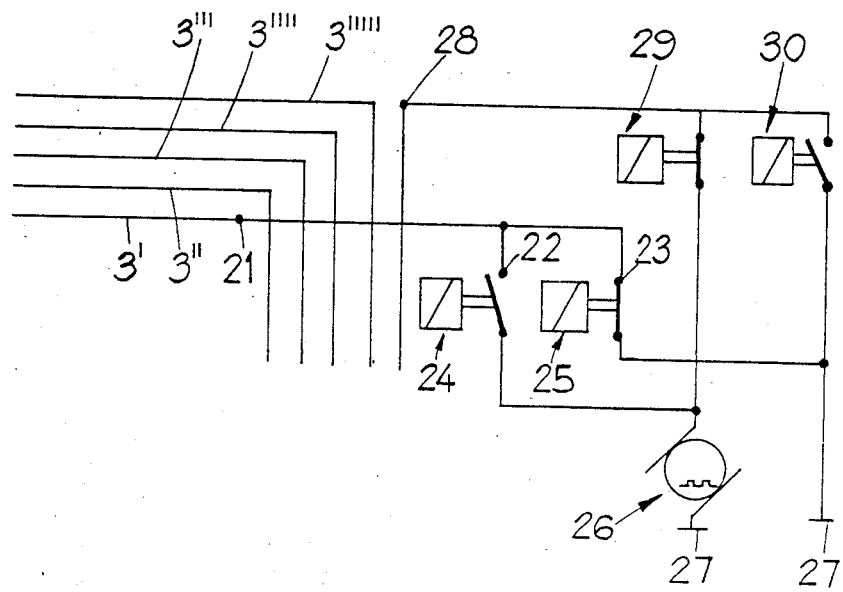
FIGS. 7 and 8 show additional detail of the circuits of FIGS. 2 and 3.
Figure 8:
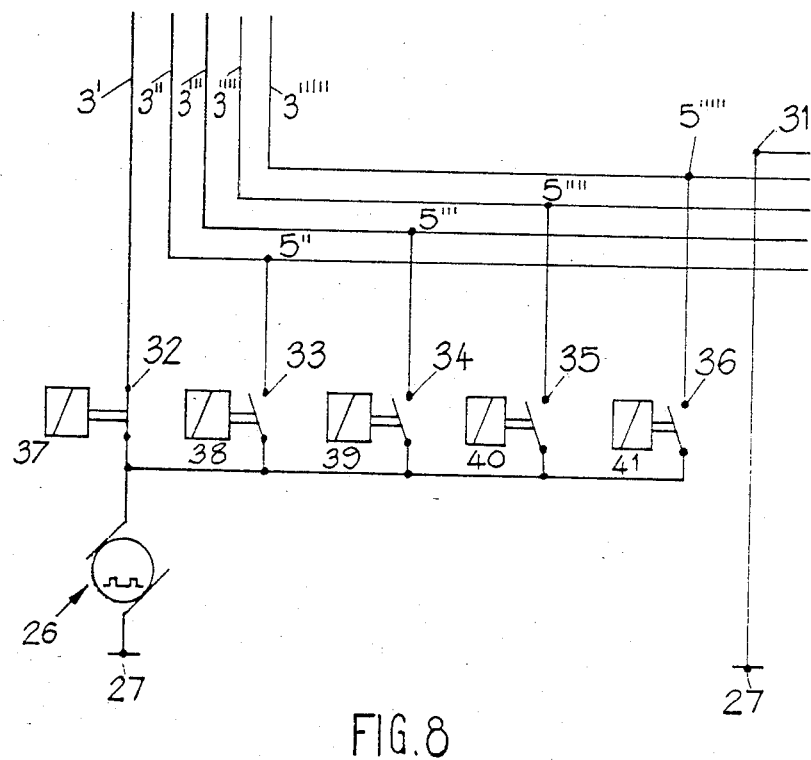

FIG. 7 shows on an enlarged scale the upper sector of the circle shown in FIG. 2, or a corresponding sector from FIG. 3 whereas FIG. 8 represents on an enlarged scale the lower sector shown in FIG. 2 or a corresponding sector from FIG. 3.

Accordingly the winding parts 3', 3", 3''', 3'''' and 3''''' are fully drawn in FIG. 7; winding part 3' terminates in a junction 21 through which a connection to contacts 22, 23 is shown in the drawing. These contacts 22, 23 are respectively associated with reed relays 24, 25, more specifically speaking, in such a manner that reed relay 24 is capable of making the connection to the generator 26 which latter generates the alternating current. Reed relay 25 on the other hand makes the connection to earth 27 to which is also connected the other output terminal of the generator 26. In the illustrated switching state therefore the junction 21 is not operatively connected to the generator.

FIG. 7 also reveals a further junction 28 which, in contrast with junction 21 representing the end of a conductor path, constitutes the start of an adjoining conductor path, namely the vertically downwardly directed conductor path in FIG. 2. This tapping point 28 is connected via a reed relay 29 to the generator 26. In this switching state the further reed relay 30 is in open position so that the connection to earth 27 otherwise made possible through the latter relay is not made in this switching state.

The switching state thus realized in FIG. 7 therefore represents in the two switching states afforded by the reed relays two relatively different state options. However, to this end it is further necessary to provide the switching arrangement according to FIG. 8. Before illustrating the modus operandi and effect of this arrangement let us consider which parts are shown in FIG. 8.

This Figure shows the sector represented in the lower circle picture of FIG. 2. Again there are five vertical winding parts 3', 3", 3''', 3'''' and 3'''''. There are also five horizontal winding parts which with the exception of 3' are in connection with the vertical winding parts. In addition to this the horizontal conductor path is characterized by a winding start or by a winding end corresponding to the tap 31 which is connected to earth 27.

The tapping points shown at 5 in FIG. 2 can be seen in FIG. 8 as junctions 5", 5''', 5'''' and 5'''''. Each of these junctions as well as winding part 3' lead to respectively one contact which contacts, counting from 3' to 5''''', carry the reference numbers 32, 33, 34, 35 and 36. These contacts are individually associated with a reed relay, respectively numbered 37, 38, 39, 40, 41. These reed relays are so branched that in each case one of them can make the connection to generator 26 of which the other output is applied to earth 27.

With the aid of these hereinbefore perceptually described switching elements one obtains, according to FIG. 8, a frequency-commutation circuit whilst FIG. 7 illustrates the same elements arranged to produce a wavelength change. The frequency change and the wavelength change may be executed simultaneously or at relatively different times, this will be determined by the objective of the test.

The frequency switching according to FIG. 8 is made in corresponding manner additionally at the same point in FIG. 2 or in FIG. 3 at which is also made the wavelength switch according to FIG. 7. This is done by making the winding part end 21 replace the generator 26 of FIG. 8 and joining the winding part 28 into connection 31 of FIG. 8. The joints of the winding parts which are between 21 and 28 continue to merge into positions 5", 5''', 5'''', 5''''' of FIG. 8.

Having now described the individual features of FIG. 7 as well as of FIG. 8, we shall now provide a statement as to why and how these switching elements of FIG. 7 and of FIG. 8 jointly produce the result that the conductor paths comprise winding parts which are mutually connectable by activation by means of switching elements in such a manner that for each frequency in several switching states wavelengths are obtained which are at the ratio of small, whole aliquant numbers.

The switching state reproduced in FIG. 7 produces the result that the conductor paths of FIG. 2 are rendered alternately by pairs current carrying or live. To this end, the switching state obtains as shown in FIG. 8.

In other words, the switching state shown in FIG. 8 i the pre-condition for the alternate pairwise current flow through the conductor paths in FIG. 7 thus as the circuit has been reproduced in the drawing. If on the other hand FIG. 7 is changed to the alternative switching state current flows alternately in triplets through the conductor paths. In this way it is possible, with FIG. 8 remaining unchanged, to switch to different states of FIG. 7 and thereby produce two different wavelengths which have a relative ratio of small whole aliquant numbers, namely a ratio of 2:3. This means that we have achieved or realized that which has been specified in the main claim.

The frequency change according to FIG. 8 is based on the fact that of several junctions 3' 5", 5''', 5'''', 5''''' one is adapted to be driven or activated by means of the reed relays 37 to 41.

The switching elements in question are, as repeatedly hereinbefore mentioned, reed relays. Such reed relays are readily accessible to the skilled man. They are commercially obtainable from the firm Hamlin. The unblocking or bias-reducing potentials of these reed relays may be 7.5 kV and current on contact may be up to 3 amps so that even heavy duty switching performance can be achieved. In the context of this invention high spacing currents are important and it is for this reason that a potential up to 7.5 kV is also on offer.

In respect of FIG. 8 basically the same statement applies as in respect of FIG. 7 bearing in mind a corresponding appropriate junctions of winding parts. These junctions of the winding parts are indicated in the complementary FIG. 3 by the additionally adopted reference numbers 21 and 28 on the one hand and on the other hand by 31 for the tap applied to mass. Furthermore, there are corresponding junctions 5'', 5''', 5'''', 5''''' as well as the winding part 3'.

In respect of the aforementioned parts of FIG. 3 the same arrangement applies as in FIG. 7 or FIG. 8 and thus also the same statement. Thus FIGS. 7 and 8 represent a complementary or additional statement in respect of FIG. 2 on the one hand and of FIG. 3 on the other.

We claim:

1. An electromagnetic transducer for the transmission and reception of ultrasonic waves in the touchless testing of flat strip and sheet metal by wavelength spectroscopy, comprising:
at least one transducer segment having a plurality of mutually parallel conductor tracks formed on a substantially plane printed circuit board in which the frequencies and wavelengths for each segment are preset in a matrix logic circuit having a short time sequence and in which said conductor tracks include windings operably connected through a set of switching elements to produce in various switching states of said elements a plurality of wavelengths being proportionally related to one another by small integral numbers.

2. An electromagnetic transducer according to claim 1, in which each one of said conductor tracks is a multiwinding track and in which said conductor tracks are relatively spaced at equi-distant intervals.

3. An electromagnetic transducer according to claim 1 in which said conductor tracks are constructed for optional variation of their polarity arrangement to function either as a coil or as a meander.

4. An electromagnetic transducer according to claim 1 in which said conductor tracks are provided with junctions spaced so as to allow the frequency response curve of said transducer to be smoothed in the operative frequency range.

5. An electromagnetic transducer according to claim 1 in which two laterally spaced overlapping segments are provided of identical configuration and in which a delay circuit is provided so that said overlapping segments can be operated with a phase difference.

6. An electromagnetic transducer according to claim 1 which is connected via its earth terminal to electrically conducting rollers formed from synthetic material and which are arranged to maintain conductive rolling contact with the workpiece under test for keeping the workpiece in spaced relationship with the transducer.

7. An electromagnetic transducer according to claim 1 in which the received signal is subjected to interference suppression by means of a digital signals detector circuit in which the received signal is applied to a first shift register together with clock pulses from a pulse generator and a comparator and to a backward counter, a second shift register being provided in series with said first shift register and both shift register outputs being fed into the comparator which is followed by said backward counter, the carry-out output of which is activated when a pre-set pulse number is exceeded.

8. An electromagnetic transducer according to claim 1 in which said conductor tracks are photolithographically structured metal lines applied by vapour-deposition on an electrically and magnetically non-conductive substrate.

9. An electromagnetic transducer according to claim 8, in which said metal lines consist of aluminum.

10. An electromagnetic transducer according to claim 8 in which said metal tracks are vapour-deposited on a thin film coated foil.

11. An electromagnetic transducer according to claim 8 in that the substrate consists of silicon-monocrystal platelets carrying an oxidation layer.

12. An electromagnetic transducer according to claim 8 in which the substrate is provided on one side thereof with said conductor tracks on the other side with said conductors which cross said conductor tracks or their winding parts.

* * * * *